(12) United States Patent
Brand et al.

(10) Patent No.: US 8,076,279 B2
(45) Date of Patent: Dec. 13, 2011

(54) CLEANSING FORMULATIONS COMPRISING NON-CELLULOSIC POLYSACCHARIDE WITH MIXED CATIONIC SUBSTITUENTS

(75) Inventors: Piet Brand, Etten-Leur (NL); Richard G. Brown, Aberdeen, MD (US); Anita N. Chan, Wilmington, DE (US); Paquita Erazo-Majewicz, Landenberg, PA (US); Jashawant J. Modi, Hockessin, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 12/576,639

(22) Filed: Oct. 9, 2009

(65) Prior Publication Data

US 2010/0093584 A1   Apr. 15, 2010

Related U.S. Application Data

(60) Provisional application No. 61/195,698, filed on Oct. 9, 2008.

(51) Int. Cl.
*C11D 1/62* (2006.01)
*C11D 3/22* (2006.01)
*A61K 8/73* (2006.01)
*A61Q 5/00* (2006.01)

(52) U.S. Cl. ........ 510/504; 510/121; 510/151; 510/330; 510/470; 510/474; 424/479; 424/481; 424/70.13; 514/54; 514/60

(58) Field of Classification Search .................. 510/121, 510/151, 330, 470, 474, 504; 424/479, 481, 424/70.13; 514/54, 60
See application file for complete search history.

(56) References Cited

U.S. PATENT DOCUMENTS

| 5,473,059 | A | 12/1995 | Yeh | |
|---|---|---|---|---|
| 2002/0172653 | A1* | 11/2002 | Cannell et al. | ............. 424/70.13 |
| 2005/0158266 | A1 | 7/2005 | Peffly et al. | |

FOREIGN PATENT DOCUMENTS

| WO | 97/26854 | 7/1997 |
|---|---|---|
| WO | 03/088932 | 10/2003 |
| WO | 2008/065537 | 6/2007 |
| WO | 2008/057425 | 5/2008 |

OTHER PUBLICATIONS

International Search Report, PCT/US2009/060164, Jul. 13, 2010.

* cited by examiner

*Primary Examiner* — Brian P Mruk
(74) *Attorney, Agent, or Firm* — Robert O'Flynn O'Brien; Joanne Mary Fobare Rossi; Wein-Wen Yang

(57) ABSTRACT

The present invention is related to the use of a non-cellulosic cationically modified polysaccharide in cleaning compositions and more particularly to a surfactant based cleansing composition comprising, a surfactant, a non-cellulosic cationically modified polysaccharide and a solvent for use in personal care composition, household care composition or an institutional care composition.

44 Claims, No Drawings

CLEANSING FORMULATIONS COMPRISING NON-CELLULOSIC POLYSACCHARIDE WITH MIXED CATIONIC SUBSTITUENTS

RELATED APPLICATIONS

This application claims the benefit of U.S. Provisional application Ser. No. 61/195,698, filed on Oct. 9, 2008, which is incorporated herein by reference in its entirety.

FIELD OF THE INVENTION

The present invention relates to cleansing formulations, particularly surfactant based formulations comprising polymer compositions, especially a surfactant based cleansing composition comprising, a surfactant, a non-cellulosic cationically modified polysaccharide and a solvent, wherein the polymer composition comprises a cationically modified polysaccharide, wherein the cationic modification comprises a mixture of at least two quaternary ammonium groups having different substituents, covalently attached to the polysaccharide backbone. The cleansing formulations are useful in personal care applications as well as household care and institutional applications.

BACKGROUND OF THE INVENTION

Polygalactomannans, polyglucomannans, and other non-cellulosic polysaccharides and their derivatives are used in various applications such as oil recovery, personal care products, textile applications, paper applications, coating applications, food applications, pharmaceutical applications, etc. Cationic polysaccharides and other polymers have been used widely in personal care, household, industrial, and institutional products to perform a function in the final product, ranging from the use of the polymer as gellants, binders, thickeners, stabilizers, emulsifiers, spreading and deposition aids, and carriers for enhancing the rheology, efficacy, deposition, aesthetics and delivery of chemically and physiologically active ingredients in personal care, (e.g., cosmetic, oral care, baby care), household, or pet care compositions. Depending on the application, the substrate can be skin, hair, or textile substrates.

Both low and high molecular weight polygalactomannans such as cationic guars, marketed under the trade names N-Hance® or Jaguar® cationic guars, are commonly used as conditioners in personal cleansing products such as shampoos, 2-in-1 or 3-in-1 conditioning shampoos and body washes, which are formulated at acidic or neutral pH values. The cationic functional group on these polymers is the hydroxypropyl trimethyl ammonium group, where all three substituent groups on the nitrogen are methyl groups containing one carbon.

Cationic polysaccharides are used in hair care products to provide conditioning to the hair. In skin care products, these same polymers can provide conditioning effects to the skin. When incorporated into detergent and fabric softening formulations, these same polymers can provide conditioning, softening, and antistatic characteristics to fabrics.

Wet and dry combability measurements are typical test methods used to measure conditioning performance in shampoo and conditioner applications. Commercial conditioning polymers in the marketplace have been reported to reduce the wet combing force experienced on combing wet hair by 30%-80% relative to the shampoo containing no polymer.

Conditioning performance in a shampoo application can also be measured by monitoring the decrease in optical transmittance of a transparent shampoo or cleansing formulation containing conditioning polymers on increasing dilution with water. The larger the drop in transmittance on dilution with water, the greater the level of deposition. The drop in transmittance or decrease in optical clarity of the formulation is associated with precipitation of the conditioning polymer from the shampoo or other cleansing formulation. The conditioning polymer can be deposited in the form of a complex with surfactants in the formulation or in an uncomplexed form.

The amount of silicone, other conditioning oils or functional materials, zinc, or other active or performance material deposited onto hair or the scalp from a shampoo or colorant system, onto skin from a cleansing or conditioning body wash, or onto fabric from a surfactant-based laundry formulation is also a measure of the conditioning performance of a conditioning polymer. The uniformity or nonuniformity of deposition of the silicone, other conditioning oils or conditioning materials, zinc, fragrance, or other "active" material can have significant impact on the perceived performance of the cosmetic formulation. The deposition profile is especially important on substrates such as: 1) hair fibers, where deposition along the fiber, from root to tip, is needed to ameliorate the damage in areas toward the tip or end of the hair fiber and to deposit color uniformly from hair coloring formulations and maintain color uniformity along the fibers; 2) on skin, especially in dry or damaged areas of the skin, where deposition of oils, other conditioning agents, active materials such as antimicrobial agents, sunscreen actives, or colorants such as self-tanning ingredients is needed to occur uniformly; and 3) on fabrics, where deposition occurs, especially on damaged or worn areas, of fabrics such as wool, cotton, polyester.

In skincare applications, skin lubricity or reduced friction or softer feel of the skin, reduced water vapor transmission and improved skin elasticity are test methods used to measure skin conditioning. In surfactant-based household cleansing product formulations where conditioning performance is desired, such as dish detergents, laundry detergents, fabric softeners, and antistatic products, conditioning refers to imparting a softer feel to fabric and eliminating static effects, eliminating fabric fiber breakage or deformation known as pilling. Imparting color retention or color vibrancy properties to fabrics is also important and can be measured.

In addition to conditioning applications, non-cellulosic cationically modified polysaccharides can also be used for rheology modification of these formulations, lather enhancement as well as for lather stability and for delivery and prolonged retention of other personal care formulation ingredients, such as fragrances, dyes, or antimicrobial compounds, on the deposition surface.

Despite the well known utility of non-cellulosic cationically modified polysaccharides as conditioning polymers in surfactant based cleansing formulations as deposition aids for conditioning oils and active treatment delivery to the hair and skin, the repeated use of these polymers can confer unwanted buildup of conditioning components, such as silicone and other oils, on the hair. This buildup is apparent as an increase in the energy needed to comb through the dry hair, and as a sticky feel to the hair. In addition, the current classes of conditioning polymers deliver more conditioning to the root end of the hair fiber, and there is a need to create polymer compositions that deliver more uniform deposition of silicone and other actives along the length of the hair fiber, to the middle section and tip of the hair fiber, where the fiber is more damaged and in need of more conditioning. Finally, in the area of antidandruff and delivery of antimicrobial active materials to the scalp, there is a need for increasing the efficiency of delivery of antimicrobial compound from surfactant systems such as shampoos and hand cleansers, as well as better targeting delivery to the scalp and skin, and maintaining it in place for prolonged activity.

SUMMARY OF THE INVENTION

The present inventors have discovered cleansing composition comprising, a surfactant, a polymer composition and a solvent. The polymer composition in the cleaning composition comprises a non-cellulosic cationically modified polysaccharide in which the cationic modification comprises a mixture of at least two quaternary ammonium groups having different combinations of alkyl, aryl, or aralkyl substituents. The least two quaternary ammonium groups are covalently attached to the polysaccharide backbone. In the non-cellulosic cationically modified polysaccharide, the substituents are attached to the nitrogen atom of the quaternary ammonium groups.

The polysaccharide composition having combinations of different quaternary ammonium groups attached to the polysaccharide backbone has been found to be useful in performing as a deposition agent with reduced buildup on hair from surfactant systems, delivering improved uniformity of silicone deposition along the hair fiber on all hair types, including damaged hair or bleached hair, delivering improved lubricity or softness to hair, as measured by dry comb and friction measurements, when delivered from silicone and nonsilicone cleansing compositions, and for improved deposition of other benefiting active materials, such as colors or dyeing agents, antidandruff agent such as zinc pyrithione, fragrance, antimicrobial materials, uv protector, sun blockers, hair growth agents etc., onto the scalp and the hair. The non-cellulosic cationically modified polysaccharide of use in the present invention can contain varying amounts of protein as part of its composition. When the substituents are alkyl groups, the alkyl chain can range in length from one carbon to thirty carbons ($C_1$ to $C_{30}$).

The improved deposition performance of this surfactant-based cleansing composition comprising the non-cellulosic cationically modified polysaccharide has been shown to translate to improved deposition of benefiting agents such as silicone, improved deposition of antidandruff particulates such as zinc and zinc pyrithione, and is expected to also translate to improved deposition of oils, coloring agents, perfumes, and other dispersed phase active materials onto hair, skin, and fabric surfaces when delivered from anionic surfactant systems, from nonionic, amphoteric or zwitterionic surfactant systems, and mixtures thereof.

Compositions which are particularly useful are prepared with amphoteric surfactants, nonionic surfactants, anionic surfactants, zwitterionic surfactants, and mixtures thereof, in addition to the polymers of the invention. Optionally, cationic surfactants can also be present in an amount of from 0.01 to about 1.0 wt %.

DETAILED DESCRIPTION OF THE INVENTION

It has been found that a non-cellulosic cationically modified polysaccharide and more particularly polygalactomannan compositions or polyglucomannan compositions that contain a mixture of cationic functionality, such as two different quaternary ammonium groups, covalently attached along the polysaccharide backbone, where the substituents attached to the nitrogen atom can be different combinations of alkyl, aryl, and aralkyl groups are useful in performing as deposition agents with reduced buildup on hair from surfactant systems, providing improved uniformity of silicone deposition along the hair fiber on all hair types, including damaged hair or bleached hair, providing improved lubricity or softness of hair, as measured by dry comb and friction measurements, when delivered from silicone and nonsilicone shampoos, and providing improved deposition of other active materials, such as colors or dyeing agents, zinc pyrithione, fragrance, antimicrobial materials such as salicylic acid, etc., onto the scalp and the hair.

The non-cellulosic cationically modified polysaccharides of use in the present invention can contain varying amounts of protein as part of their composition. The non-cellulosic cationically modified polysaccharides can deposit with high efficiency on substrates such as hair, skin, teeth, oral mucosa, or textile fabrics and can impart great conditioning benefits to the substrates. Upon deposition onto the substrate, the non-cellulosic cationically modified polysaccharide can also deposit other ingredients, which improve the condition or enhance the characteristics of the substrate. The non-cellulosic cationically modified polysaccharides of use in the present invention also have potential for conditioning skin from cleansing formulations or moisturizing formulations, since these polymers may also better deliver the oil phase typically used in creams and lotions.

Surprisingly, it has been found that non-cellulosic cationically modified polysaccharides and more particularly polygalactomannan compositions or polyglucomannan compositions, that contain at least two quaternary ammonium groups having different substituents, covalently attached to the polysaccharide backbone, are useful in performing as deposition agents with reduced buildup on hair from surfactant systems, improved uniformity of silicone deposition along the hair fiber on all hair types, including damaged hair or bleached hair, improved lubricity or softness of hair, as measured by dry comb and friction measurements, when delivered from silicone and nonsilicone shampoos, and for improved deposition of other active materials, such as colors or dyeing agents, zinc pyrithione, fragrance, antimicrobial materials, etc., onto the scalp and the hair. The non-cellulosic cationically modified polysaccharides of use in the present invention can contain varying amounts of protein as part of their composition. These polymers can deposit with high efficacy and impart uniformity to deposits applied onto hair/skin and can impart great conditioning benefits to keratin substrates. Such polymers impart other benefits in hair styling, body lotions and sunscreens due to hydrophobic film formation on keratin substrates that would act as a barrier between the surfaces and the surrounding atmosphere.

In accordance with the present invention, non-cellulosic cationically modified polysaccharides have a mixture of cationic substituents. The cationic degree of substitution (DS) of each substituent having a lower limit of about 0.0001 and an upper limit of about 3.0. Preferably, the lower limit of the cationic DS is 0.001, and more preferably 0.002 and even more preferably 0.003. Preferably, the upper limit of the cationic DS is 3.0, more preferably 1.0, and even more preferably 0.25 to 0.35. The non-cellulosic cationically modified polysaccharide has a weight average molecular weight (Mw) with a lower limit of about 10,000 and an upper limit of about 2,000,000. Preferably, the non-cellulosic cationically modified polysaccharide has a weight average molecular weight (Mw) with a lower limit of about 200,000 and an upper limit of about 1,500,000, more preferably with a lower limit of about 300,000 and an upper limit of about 1,000,000.

In accordance with present invention, the non-cellulosic cationically modified polysaccharide, and more preferably the cationic polygalactomannan or cationic derivatized polygalactomannan can have a crosslinker present, such as boron, glyoxal, or other treatment that renders the non-cellulosic cationically modified polysaccharide readily dispersible without clumping in water. The crosslinker content can be less than 5 wt % per gram of non-cellulosic cationically modified polysaccharide, and preferably less than 1 wt %. The crosslinker may also be of the type that can form irreversible covalent crosslinks with the polymers of the invention, producing a product with more swelling performance in aqueous systems.

The polygalactomannan gum from which the non-cellulosic cationically modified polysaccharide of the present invention is derived is selected from the group consisting of guar, locust bean, tara gum, honey locust, cassia, fenugreek, and flame tree. Other non-cellulosic polysaccharides useful in the present invention include xanthan gum, gellan gum, welan gum, rhamsan gum, konjac, mannan, gum arabic, soy polysaccharide, xylofructose gums, polyglucose (starch), and tamarind gum.

The alkyl group substituents have an alkyl chain length in a range from one carbon to thirty carbon. Preferably the alkyl group substituents on a first quaternary ammonium group will have an alkyl chain length of one carbon. The cationic functionalities of the non-cellulosic cationically modified polysaccharide can be added to the backbone by known methods. For example, the non-cellulosic polysaccharide, such as polygalactomannan can be reacted for a sufficient time and at a sufficient temperature with a first quaternary ammonium alkylating reagent, such as 3-chloro-2-hydroxypropyltrimethylammonium chloride, and 2,3-epoxy-propyltrimethylammonium chloride. Preferred examples include a combination of two glycidyltrialkylammonium salts or 3-halo-2-hydroxypropyltrialkylammonium salts where the first quaternary ammonium reagent is glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, 3-chloro-2-hydroxypropylethyldiethylammonium chloride and their corresponding bromides and iodides; and quaternary ammonium compounds such as halides of imidazoline ring containing compounds.

The second quaternary ammonium reagent is selected from reagents which contain at least one alkyl, aralkyl, aryl, or alkenyl group on the nitrogen where the alkyl group can be, for example, a straight or branched chain alkyl group having 1 to 30 carbon atoms. Exemplary modifying radicals are propyl-, butyl-, pentyl-, 2-ethylhexyl, octyl, cetyl, octadecyl, dodecyl, methylphenyl, and docosapolyenoic glycidyl ether.

At least one group on the second quaternary ammonium group has an alkyl chain length in a range from one carbon to thirty carbons. Preferably the will have a carbon chain length greater than 2 carbons, preferably greater than 6 carbons, preferably greater than 8 carbons in length, preferably an alkyl chain length of 12 carbons, 18 carbons or twenty-two carbons. Such groups on the second quaternary ammonium group include glycidyldodecyldimethylammonium chloride, glycidyldodecyldiethylammonium chloride, glycidyldodecyldipropylammonium chloride, glycidyloctadecyldimethylammonium chloride, glycidyldiethylmethylammonium chloride, and their corresponding bromides and iodides; 3-chloro-2-hydroxypropyldodecyldimethylammonium chloride, 3-chloro-2-hydroxypropyldodecyldiethylammonium chloride, 3-chloro-2-hydroxypropyldodecyldipropylammonium chloride, 3-chloro-2-hydroxypropyloctadecyldimethylammonium chloride, and their corresponding bromides and iodides; and quaternary ammonium compounds such as halides of imidazoline ring containing compounds. The substituents on the quaternary ammonium nitrogen moiety may include at least one straight or branched hydrocarbon alkyl moiety having 1 to 30 carbon atoms, aryl groups, aralkyl groups, hydroxyalkyl wherein the alkyl represents a straight or branched hydrocarbon moiety having 1 to 30 carbon atoms (e.g., hydroxymethyl, hydroxyethyl, hydroxypropyl, hydroxybutyl).

The non-cellulosic cationically modified polysaccharide may also contain other substituent groups such as nonionic substituents, i.e., hydroxyalkyl wherein the alkyl represents a straight or branched hydrocarbon moiety having 1 to 30 carbon atoms (e.g., hydroxymethyl hydroxyethyl, hydroxypropyl, hydroxybutyl), alkyl, aralkyl, or aryl groups wherein the alkyl represents a straight or branched hydrocarbon moiety having 1 to 30 carbon atoms, or anionic substituents, such as carboxymethyl groups, sulfonic acid groups, or phosphonic acid groups are optional. These optional substituents are linked to the non-cellulosic polysaccharide by the reaction with reagents such as for example (1) alkylene oxides (e.g., ethylene oxide, propylene oxide, butylene oxide) to obtain hydroxyethyl groups, hydroxypropyl groups, or hydroxybutyl groups, or with (2) chloromethyl acetic acid to obtain a carboxymethyl group, or with (3) chloroethylsulfonic acid to obtain a sulfonic acid group, or with (4) chloroethylphosphonic acid to obtain a phosphonic acid group. The process for preparing a derivatized non-cellulosic polysaccharide is well known in the art. The non-cellulosic cationically modified polysaccharide may also contain a mixture of one or more other substituent groups such as nonionic, anionic and cationic substituents.

These non-cellulosic cationically modified polysaccharides may also be useful as film-formers and co-deposition agents onto the surfaces of hair, skin, and textiles, aiding in protection of the hair, skin, and textile substrates from moisture-loss, aiding deposition of sunscreens and subsequent protection of these substrates from UV radiation, enhancing deposition of fragrance or flavor onto substrates and entrapping fragrance and flavor leading to their improved longevity on these substrates, or aiding deposition of antimicrobial reagents and other active personal care ingredients, resulting in improved longevity of the active on the substrate. In addition, these non-cellulosic cationically modified polysaccharides find use in oral care applications such as dentifrices and denture adhesives to deliver prolonged flavor retention and flavor release. Prolonged release of antimicrobial and biocide agents from these non-cellulosic cationically modified polysaccharides may also find use in household and personal care applications, such as skin and hair treatment formulas and in oral care applications such as dentifrice, denture adhesives, and whitening strips. These non-cellulosic cationically modified polysaccharides may also be useful in the enhancement of the antimicrobial performance of antimicrobial and biocide agents.

In accordance with this invention, the conditioning benefits of non-cellulosic cationically modified polysaccharides and more particularly cationically modified polygalactomannan compositions or cationically modified polyglucomannan compositions are demonstrated as conditioning agents in personal care compositions such as hair care and skin care compositions. Performance is also expected in oral care compositions, such as toothpastes, oral rinses, anticaries mouth rinses, and antimicrobial mouthwashes as well as household care compositions, such as laundry cleaner and softener products for textile substrates and hard surface cleaner products.

In accordance with the present invention, the functional system substrate is defined as a material that is related to personal care and household care applications. In personal care, the substrate can be skin, hair, teeth, and mucous membranes. In household care products, the substrate can be hard surfaces such as metals, marbles, ceramics, granite, wood, hard plastics, and wall boards or soft surfaces such as textiles and fabrics.

Any water soluble non-cellulosic polysaccharides and more particularly polygalactomannan, polyglucomannan, can be used as the backbone to form the non-cellulosic cationically modified polysaccharide of use in the present invention. Thus, e.g., agar, dextran, polyglucose (starch), polyglucomannan polymers, polyaminoglycan (chitosan), xanthan polymers, and other non-cellulosic polysaccharides can all be modified. The non-cellulosic polysaccharides of use in this invention have a sufficient degree of two different quaternized ammonium group substituents to render the polymers effective in delivering improved conditioning aspects to hair and skin substrates, improved uniformity of silicone deposition onto the substrate, and positive sensory aspects to the substrate, especially hair, skin, and fabrics.

The preferred non-cellulosic polysaccharide backbone is polygalactomannan, such as guar, locust bean gum, tara gum, and other non-cellulose based polysaccharides, such as galactomannan or glucomannan polymers, e.g., konjac gum or aloe gum.

The quaternary ammonium groups can be attached to the non-cellulosic polysaccharide backbone via an ether, ester, or urethane linkage. Ether is the preferred linkage as the reagents most commonly used to effect etherification because it is readily obtainable; the reaction is similar to that commonly used for the initial etherification, and the reagents used in the reaction are usually more easily handled than the reagents used for modification via the other linkages. The resulting linkage is also usually more resistant to further reactions.

The non-cellulosic cationically modified polysaccharide of use in the present invention is an essential ingredient of the cleansing composition. A second essential ingredient of the cleansing composition is a nonionic, anionic, amphoteric or mixture of these surfactants that can be either soluble or insoluble in the composition. An optional ingredient is a compatible solvent which may also be used in the cleansing composition that can be either a single solvent or a blend of solvents.

Examples of the surfactants are anionic, nonionic, zwitterionic, or amphoteric type of surfactants, and blends thereof. The anionic, nonionic, zwitterionic, or amphoteric surfactant can be soluble or insoluble in the present invention and (when used) is present in the composition in the amount of from 0.01 to about 50 wt % by weight of the cleansing composition. Synthetic anionic surfactants include alkyl and alkyl ether sulfates. Optionally, cationic surfactants can also be present in an amount of from 0.01 to about 1.0 wt %.

Nonionic surfactants, can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Nonionic surfactants such as those marketed under the trade name Surfynol®, available from Air Products and Chemicals, Inc. are also useful in this invention.

Zwitterionic surfactants are exemplified by those which can be broadly described as derivative of aliphatic quaternary ammonium, phosphonium, and sulfonium compounds in which the aliphatic radicals can be straight or branched chain, and wherein one of the aliphatic substituents contains from about 8 to about 18 carbon atoms and one contains as anionic water-solubilizing group, e.g., carboxy, sulfonate, sulfate, phosphate, or phosphonate.

Examples of amphoteric surfactants which can be used in the vehicle systems of the cleansing composition of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

According to the present invention, the solvent used in the system should be compatible with the other components of the cleansing composition. Examples of the solvents that may be used in the present invention are water, water-lower alkanols mixtures, and polyhydric alcohols having from 3 to 6 carbon atoms and from 2 to 6 hydroxyl groups. Preferred solvents are water, propylene glycol, water-glycerine, sorbitol-water, and water-ethanol. The solvent (when used) in the present invention is present in the composition at a level of from 0.1% to 99% by weight of the composition.

In certain instances, an active ingredient or benefiting agent is optional because the dissolved polymer can be the active ingredient component. An example of this is the use of the polymer in an aqueous solution as a conditioner for hair or skin conditioning, as a fabric conditioner, or as an antimicrobial agent. However, when an additional active ingredient or benefit agent is needed, it must provide some benefit to the user or the user's body.

In accordance with the present invention, the cleansing composition may be a personal care product, a household care product or an institutional care product. When the cleansing composition is a personal care product that contains at least one active personal care ingredient or benefit agent, the personal care active ingredient or benefit agent includes, but is not limited to, analgesics, anesthetics, antibiotic agents, antifungal agents, antiseptic agents, antidandruff agents, antibacterial agents, vitamins, hormones, anti-diarrhea agents, corticosteroids, anti-inflammatory agents, vasodilators, kerolytic agents, dry-eye compositions, wound-healing agents, anti-infection agents, UV absorbers, as well as solvents, diluents, adjuvants and other ingredients such as water, ethyl alcohol, isopropyl alcohol, propylene glycol, higher alcohols, glycerine, sorbitol, mineral oil, preservatives, surfactants, propellants, fragrances, essential oils, and viscosifying agents.

Personal care compositions include hair care, skin care, sun care, nail care, and oral care compositions. Examples of active personal care ingredients or benefit agents that may suitably be included, but not limited to, in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;

3) Emollients, such as isopropylmyristate, silicone materials, mineral oils and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keep the skin moist by either adding moisture or preventing from evaporating from the skin;

7) Sunscreen active ingredients that protect the skin and hair from UV and other harmful light rays from the sun. In accordance with this invention a therapeutically effective amount will normally be from 0.01 to 10% by weight, preferable 0.1 to 5% by weight of the composition;

8) Hair treatment agents, that condition the hair, cleanse the hair, detangles hair, acts as styling agent, volumizing and gloss agents, color retention agent, anti-dandruff agent, hair growth promoters, hair dyes and pigments, hair perfumes, hair relaxer, hair bleaching agent, hair moisturizer, hair oil treatment agent, and antifrizzing agent; and 9) Oral care agents, such as dentifrices and mouth washes, that clean, whiten, deodorize and protect the teeth and gum.

In accordance with the present invention, when the cleansing composition is a household care compositions, this household care compositions includes a non-cellulosic cationically modified polysaccharide, wherein the cationic modification comprises a mixture of at least two quaternary ammonium groups having different substituents, covalently attached to the polysaccharide backbone and at least one active household care ingredient or benefit agent. The household care active ingredient or benefit agent must provide some benefit to the user. Examples of active ingredients that may suitably be included, but not limited to, according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactant that generates foam or lather;

4) Pet deodorizer or insecticides such as pyrethrins that reduces pet odor;

5) Pet shampoo agents and actives, whose function is to remove dirt, foreign material and germs from the skin and hair surfaces;

6) Industrial grade bar, shower gel, and liquid soap actives that remove germs, dirt, grease and oil from skin, sanitizes skin, and conditions the skin;

7) Disinfecting ingredients that kill or prevent growth of germs in a house or public facility;

8) A laundry softener active, which reduces static and makes fabric feel softer;

9) Laundry or detergent or fabric softener ingredients that reduce color loss during the wash, rinse, and drying cycle of fabric care;

10) Toilet bowl cleaning agents, which remove stains, kills germs, and deodorizes;

11) Laundry prespotter actives which helps in removing stains from clothes; and

12) Fabric sizing agent which enhances appearance of the fabric.

The above lists of personal care and household care active ingredients or benefit agents are only examples and are not complete lists of active ingredients that can be used. Other ingredients that are used in these types of products are well known in the industry. In addition to the above ingredients conventionally used, the composition according to the present invention can optionally also include ingredients such as a colorant, preservative, antioxidant, nutritional supplements, alpha or beta hydroxy acid, activity enhancer, emulsifiers, functional polymers, viscosifying agents (such as salts, i.e., NaCl, $NH_4Cl$, and KCl, water-soluble polymers, i.e., hydroxyethylcellulose and hydroxypropylmethylcellulose, and fatty alcohols, i.e., cetyl alcohol), alcohols having 1-6 carbons, fats or fatty compounds, antimicrobial compound, zinc pyrithione, silicone material, hydrocarbon polymer, emollients, oils, surfactants, medicaments, flavors, fragrances, suspending agents, and mixtures thereof.

In accordance with the present invention, examples of functional polymers that can be used in blends with the non-cellulosic cationically modified polysaccharide of this invention include water-soluble polymers such as acrylic acid homopolymers such as Carbopol® polymer and anionic and amphoteric acrylic acid copolymers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; acrylamide homopolymers and cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and non-ionic, anionic, hydrophobic, amphoteric, and cationic polysaccharides such as xanthan, chitosan, starch, carboxymethyl guar, alginates, gum arabic, nonionic, cationic, anionic, and amphoteric guar polymers such as hydroxypropyl guar, hydrophobic guar polymers, carboxymethyl guar hydroxypropyltrimethylammonium chloride, guar hydroxypropyltrimethylammonium chloride, and hydroxypropyl guar hydroxypropyltrimethylammonium chloride.

In accordance with the invention, the silicone materials which can be used are polyorganosiloxanes that can be in the form of polymers, oligomers, oils, waxes, resins, or gums or polyorganosiloxane polyether copolyols, amodimethicones, cationic polydimethylsiloxane materials and any other silicone material that is used in personal care compositions, household care compositions or institutional care compositions.

The non-cellulosic cationically modified polysaccharides of use in this invention can be used as conditioning agents in 2-in-1 shampoos, body lotions, sunscreens, antifrizz and hair styling formulations. The non-cellulosic cationically modified polysaccharides of use in this invention can also be used to improve hair volume, manageability, hair repair, or color retention, skin moisturization and moisture retention, fragrance retention, sunscreen longevity on hair, skin, and fabrics, flavor enhancement and antimicrobial performance in oral care applications, and improve fabric abrasion resistance and colorfastness in household applications.

For a more detailed understanding of the invention, reference can be made to the following examples which are intended as further illustrations of the invention but are not to be construed in a limiting sense. All parts and percentages are by weight unless stated otherwise.

EXAMPLES

Comparative Examples 1-5 (Table 1)

Cationic Guar Preparation

Cationic guar was prepared by known procedures, using borax or glyoxal as a crosslinking agent. A general procedure is described below. While any purity guar splits can be used, the examples used single purified splits.

Guar splits, water, borax, 3-chloro-2-hydroxypropyltrimethylammonium chloride (Quat 188) and sodium hydroxide (see amounts in Table 1) were mixed in a stirred reactor under nitrogen. The reactor was purged with nitrogen and vented to remove oxygen. The reaction was conducted at a temperature between 40-60° C. for 0.5-3.0 hours. After cooling, the product was washed with water to remove salts and impurities, filtered, dried and ground to a powder.

In Comparative Examples 2 and 5, and Example of the invention 12, polymer degradation using hydrogen peroxide was conducted at 45-55° C. for 1.5 hours prior to the quat reaction.

In Comparative Example 4, glyoxal crosslinking, via procedure referenced in WO 2008/057425 A1, was used instead of borax crosslinking. Comparative Example 4A is a scaled up version of Comparative Example 4 in the plant.

TABLE 1

| Wt % Active | Ex 1 | Ex 2 | Ex 3 | Ex 4 | Ex 5 |
|---|---|---|---|---|---|
| | | Parts by Weight | | | |
| Guar Splits | 100 | 100 | 100 | 100 | 100 |
| Water | 46 | 38 | 51 | 51 | 14 |
| Borax | 0.3 | 0.9 | 0.3 | — | 1.1 |
| NaOH (25%) | 44 | 30 | 32 | 34 | 63 |
| Quat 188 (65%) | 48 | 30 | 33 | 91 | 80 |
| $H_2O_2$ (30%) | — | 3 | — | — | 3 |
| Glyoxal (40%) | — | — | — | 8 | — |
| Acetic Acid (100%) | — | — | — | 26 | — |

TABLE 2

| Wt % Active | Ex 8 | Ex 9 | Ex 13 | Ex 14 | Ex 15 |
|---|---|---|---|---|---|
| | | Parts by Weight | | | |
| Precursor | 100 | 100 | 100[a] | 100[b] | 100[c] |
| Water | 160 | 160 | 160 | 160 | 160 |
| NaOH (25%) | 44 | 48 | 100 | 100 | 100 |
| Quat 188 (65%) | — | — | 65 | 65 | 65 |
| Quab 342 (40%) | 12 | 24 | 71 | 71 | 71 |

[a]Techol A;
[b]Techol CDT,
[c]Techol MF

The compositions and aqueous viscosity for the polymers of Comparative Examples 1-5 are shown in Table 3.

TABLE 3

Polymer Compositions and Aqueous Solution Viscosity

| Example | Comparative Example | | Trimethyl-ammonium Quat Cationic DS | Alkyl dimethyl ammonium Quat Cationic DS | Polymer Aqueous 1.0% Viscosity/cps |
|---|---|---|---|---|---|
| 1[a] | X | 1.5% protein | 0.2 | — | 4200 |
| 2[b] | X | 1.5% protein | 0.14 | — | 45 |
| 3[c] | X | 1.5% protein | 0.14 | — | 4500 |
| 4 | X | 1.5% protein | 0.39 | — | 1920 |
| 4a[d] | X | | 0.33 | — | |
| 5 | X | 1.5% protein | 0.32 | — | 86 |
| 6 | Example of the Invention | 1.5% protein | 0.18 | 0.002 (alkyl = C12) | 1800 |
| 6A | Example of the Invention | | 0.17 | 0.005 (alkyl = C18) | 3470 |
| 7 | Example of the Invention | 1.5% protein | 0.17 | 0.008 (alkyl = C12) | 3270 |
| 8 | Example of the Invention | 1.5% protein | 0.19 | 0.002 (alkyl = C12) | 60 |
| 9 | Example of the Invention | 1.5% protein | 0.19 | 0.005 (alkyl = C12) | 30 |
| 10 | Example of the Invention | 1.5% protein | 0.25 | 0.006 (alkyl = C12) | 1880 |
| 11 | Example of the Invention | 1.5% protein | 0.29 | 0.003 (alkyl = C12) | 2420 |
| 11A | Example of the Invention | | 0.32 | 0.003 (alkyl = C12) | 2880 |
| 11B | Example of the Invention | | 0.33 | 0.002 (alkyl = C18) | 3440 |
| 11C | Example of the Invention | | 0.33 | 0.004 (alkyl = C18) | 2770 |
| 11D | Example of the Invention | | 0.32 | 0.004 (alkyl = C18) | 2740 |
| 11E | Example of the Invention | | 0.37 | 0.007 (alkyl = C18) | 3650 |
| 11F | Example of the Invention | | 0.28 | 0.001 (alkyl = C18) | 1960 |
| 12 | Example of the Invention | 1.5% protein | 0.34 | 0.002 (alkyl = C12) | 50 |
| 13 | Example of the Invention | 7-12% protein | 0.21 | 0.002-0.005 (alkyl = C12) | 1440 |

TABLE 3-continued

Polymer Compositions and Aqueous Solution Viscosity

| Example | Comparative Example | Trimethyl-ammonium Quat Cationic DS | Alkyl dimethyl ammonium Quat Cationic DS | Polymer Aqueous 1.0% Viscosity/cps |
|---|---|---|---|---|
| 14 | Example of the Invention 5-7% protein | 0.209 | 0.002-0.006 (alkyl = C12) | 1600 |
| 15 | Example of the Invention 18-21% protein | 0.321 | 0.002-0.007 (alkyl = C12) | 200 |

Examples 6, 7, 9, 10, 11, 11a

Non-Cellulosic Cationically Modified Polysaccharide of Use in this Invention

A cationic guar was prepared similarly to Comparative Example 1, with the addition of varying amounts of a 40% aqueous solution of 3-chloro-2-hydroxypropyldimethyldodecylammonium chloride (10-57 parts), 3-chloro-2-hydroxypropyltrimethylammonium chloride (36-80 parts), and the corresponding amount of caustic. The reaction was conducted at 40-65° C. for 1.5-3.0 hours. Purification was carried out as described for Comparative Example 1. The reaction product compositions are shown in Table 3 as Examples 6, 7, 9, 10 and 11a. Example 11 and 12 were prepared similarly to Comparative Example 5, with the addition of 22 parts of a 40% aqueous solution of 3-chloro-2-hydroxypropyldimethyldodecylammonium chloride.

Examples 6a, 11b-11f

Non-Cellulosic Cationically Modified Polysaccharide of Use in this Invention

A cationic guar was prepared similarly to Comparative Example 1, with the addition of 23 parts of a 40% aqueous solution of 3-chloro-2-hydroxypropyldimethyloctadecylammonium chloride, 1 part of Tetrabutyl ammonium chloride and 31 parts of 25% caustic prior to the addition of 68 parts of 3-chloro-2-hydroxypropyltrimethylammonium chloride and another 24 parts of 25% caustic. The reaction product compositions are shown in Table 3 as Examples 11c and 11e.

A cationic guar was prepared similarly to Comparative Example 4, with the addition of varying amounts of a 40% aqueous solution of 3-chloro-2-hydroxypropyldimethyloctadecylammonium chloride (11-22 parts), Tetrabutyl ammonium chloride (0.5-1 part) and 25% caustic (30 parts) prior to the addition of 3-chloro-2-hydroxypropyltrimethylammonium chloride (29-68 parts) and additional caustic (2-24 parts). The reaction product compositions are shown in Table 3 as Examples 6a, 11b and 11d.

A cationic, hydroxypropyl guar was prepared similarly to Comparative Example 1 using a hydroxypropyl guar as the precursor and the addition of 27 parts of a 40% aqueous solution of 3-chloro-2-hydroxypropyldimethyloctadecylammonium chloride, 1 part of Tetrabutyl ammonium chloride and 28 parts of 25% caustic prior to the addition of 80 parts of 3-chloro-2-hydroxypropyltrimethylammonium chloride and another 28 parts of 25% caustic. The reaction product composition is shown in Table 3 as Example 11f.

Examples 8, 13, 14 and 15

Non-Cellulosic Cationically Modified Polysaccharide Of Use in this Invention

Supercol® U guar powder (available from Hercules Incorporated) or other polysaccharide powders were added to an aqueous isopropanol (IPA) mixture (84% IPA) in a stirred reactor under nitrogen at a slurry concentration of 11%. The reactor was purged with nitrogen and vented to remove oxygen. The reaction was conducted at a temperature between 30-60° C. for 3-4 hrs after addition of 3-chloro-2-hydroxypropyldimethyldodecylammonium chloride (40% aqueous solution) and 3-chloro-2-hydroxypropyltrimethylammonium chloride (a 65% aqueous solution), followed by 25% sodium hydroxide. The reaction was cooled to room temperature, neutralizing the pH to 7 with acetic acid.

The amount of 3-chloro-2-hydroxypropyldimethyldodecylammonium chloride 40% aqueous solution and 3-chloro-2-hydroxypropyltrimethylammonium chloride (a 65% aqueous solution) was varied to generate the product in Examples 13, 14, 15, as shown in Table 3

For Example 8, N-Hance 3215® cationic guar powder (available from Hercules Incorporated) was used as the starting material, and only 3-chloro-2-hydroxypropyldimethyldodecylammonium chloride (40% aqueous solution) was added to the reaction.

The products were washed with aqueous acetone to remove salts and impurities. A sample of the purified product was dried and ground to determine the moisture content and cationic degree of substitution by known NMR methods.

For Examples 13, 14, and 15, Techol A, Techol CDT, and Techol MF guar, (available from Lucid Colloids Ltd. 401A, Navbharat Estates, Zacharia Bunder Road, Sewri (West), Mumbai, INDIA), respectively, were used as the starting material in place of Supercol® U guar. The reaction product compositions are shown in Table 3 as Examples 13, 14 and 15.

Comparative Example 16

Control Shampoo—No Polymer

The combing performance and silicone deposition performance of the shampoo composition containing no polymer is shown in Table 5 as Comparative Example 16.
Demonstration of Conditioning Performance of Products of the Invention The use of the non-cellulosic cationically modified polysaccharide materials of the invention of Examples 6-15 in a conditioning shampoo formulation was demonstrated by preparing non-silicone and silicone shampoo formulations as described below in the section titled Shampoo Preparation, using the shampoo premix composition in Table 4.
Shampoo Preparation A The conditioning shampoo formulations in Table 5 were prepared by combining 73 parts by weight (pbw) of the surfactant premix composition shown in Table 4 with 6.7 pbw deionized water and 13.3 pbw of the non-cellulosic cationically modified polysaccharide of use in the invention, as a 1.5 wt % aqueous solution, using a Caframo overhead mechanical stirrer with a dispersion blade, stirring at 600 rpm. After allowing the composition to mix for 45 minutes at ambient temperature, the formulation was allowed to remain at ambient temperature overnight. The viscosity and pH value of the formulation was recorded, with pH values ranging from 5.5-6.0.

At this time, 3 pbw of a silicone emulsion (Dow Corning® 1784 emulsion, available from Dow Corning Corporation) was added to the formulation for silicone shampoo examples, and mixing was continued for an additional 15 minutes. 4 pbw of a sodium chloride salt solution (25 wt %) was then added to the shampoo, and stirring commenced for an additional 15 minutes. For non-silicone shampoo examples, the silicone was replaced with 3 pbw water. The shampoo compositions were maintained at ambient temperature overnight, and the viscosity of each shampoo was measured using a Brookfield LVT viscometer with a Brookfield LVT viscometer, spindle 4, at 30 rpm.

Shampoo Preparation B

A second series of shampoos were prepared with and without the silicone microemulsion (Dow Corning® 1784 emulsion, available from Dow Corning Corporation) using the premix in Table 4 with 0.4 pbw carbomer (Carbopol® 980, available from Lubrizol Corporation). The control shampoo containing no polymer and no silicone was prepared from this formula and its conditioning performance was compared with the nonsilicone shampoo containing the comparative control polymer in example 4a and the polymer of the invention, example 11c in Table 3 and polymers in Examples 4a, Wet comb performance and dry friction measurements Examples 2.4 pbw of a silicone emulsion (Dow Corning® 1784 emulsion, available from Dow Corning Corporation) was added to the formulation for silicone shampoo examples in Table 4.

TABLE 4

| Surfactant Premix | Lot # | Actual Amount (g) | % by weight |
|---|---|---|---|
| Standapol ES-2 | U46A027021 | 529.61 | 66.20 |
| Amphosol CA | 7107345 | 73.66 | 9.21 |
| DI Water | — | 192.80 | 24.10 |
| Glydant ® | — | 4.00 | 0.50 |

1. Standapol ES-2 sodium laureth sulfate (2EO) Cognis
2. Amphosol CA cocamidopropyl betaine, Stepan Chemical Co.
3. Glydant preservative: Lonza Chemical Co.

Conditioning Performance Measurements-Deposition Measurements

In order for a conditioning shampoo to perform on hair, deposition of a material must occur, to reduce interfiber friction in the wet and dry states, reduce static on the hair in the dry state, reduce tangling of the hair fibers in the wet and dry states, and impart a silky, soft feel to the hair in the dry state.

The deposition performance of the polymers of this invention is demonstrated in Table 5 in the columns labeled "Dilution Deposition". The dilution of the shampoo with water at various ratios of water/shampoo produces a phase separation of the polymer-surfactant complex. This phase separation is visualized by following the reduction in % transmittance of the shampoo @ 600 nm wavelength using a UV-Vis spectrophotometer. The lower the dilution ratio and the lower the % Transmittance translate into more polymer complex depositing onto the hair, skin, or scalp. In a silicone or antidandruff formulation, the lower dilution ratio and lower % transmittance translate into more silicone and other actives depositing onto the hair and scalp. Examples 17-21 in Table 5 demonstrate the dilution deposition performance for comparative Examples 1-5 from Table 3, and Examples 22-29 in Table 5 demonstrate the dilution deposition performance for the Examples of the polymers of use in the Invention, Examples 6-15 in Table 3, relative to the control shampoo in Comparative Example 16 in Table 5, which does not show dilution deposition performance.

Table 5 contains the dilution deposition performance and comb energy reduction performance of polymers in Table 3 in a non silicone shampoo containing the ingredients in Table 4, with and without carbomer.

TABLE 5

| | Polymer in | | Dilution Deposition | | Comb Energy on Bleached European medium brown Hair | | Comb Energy on European medium brown Virgin Hair | |
| | | | Dilution ratio(Parts | Dilution Minimum/(% | | | | |
| Example | Table 3 Example | Comparative Example | Water/Parts Shampoo) | transmittance @600 nm) | wet Comb E/gf-mm | Dry Comb E/gf-mm | wet Comb E/gf-mm | Dry Comb E/gf-mm |
|---|---|---|---|---|---|---|---|---|
| 17 | 1 | X | 2.5 | 18.1 | | | | |
| 18 | 2 | X | 7.5 | 74.5 | 15990 | 1692 | 12577 | 3904 |
| 19 | 3 | X | 2.5 | 35 | 20489 | 1570 | 14477 | 3144 |
| 20 | 4 | X | 1 | 2.39 | | | | |
| 20a | 4a | X | carbomer formula | | 13443 | | 3566 | |
| 21 | 5 | X | 2.5 | 11.1 | | | | |
| 22 | 6 | Example of the Invention | 5 | 43.5 | | | | |
| 23 | 7 | Example of the Invention | 5 | 50 | 17770 | 1460 | 11817 | 3873 |
| 24 | 8 | Example of the Invention | 2.5 | 24.9 | | | | |
| 25 | 9 | Example of the Invention | 2.5 | 23.7 | | | | |
| 26 | 10 | Example of the Invention | 2.5 | 22.2 | | | | |
| 27 | 11 | Example of the Invention | 1 | 5.1 | | | | |
| 27a | 11c | Example of the Invention | carbomer formula | | 9196 | | 2631 | |

TABLE 5-continued

| | | | Dilution Deposition | | Comb Energy on Bleached European medium brown Hair | | Comb Energy on European medium brown Virgin Hair | |
|---|---|---|---|---|---|---|---|---|
| Example | Polymer in Table 3 Example | Comparative Example | Dilution ratio(Parts Water/Parts Shampoo) | Dilution Minimum/(% transmittance @600 nm) | wet Comb E/gf-mm | Dry Comb E/gf-mm | wet Comb E/gf-mm | Dry Comb E/gf-mm |
| 28 | 13 | Example of the Invention | 5 | 52.4 | | | | |
| 29 | 14 | Example of the Invention | 2.5 | 3738 | | | | |
| 30 | 15 | Example of the Invention | 2.5 | 50.3 | | | | |
| 16 | No Polymer Control | | No Deposition | 99.5 | 46689 | | 15479 | |
| 16a | No Polymer Control | | carbomer formula | | 20987 | | 3997 | |

Wet and Dry Combing Performance Measurements

Wet and dry combability measurements are typical test methods used to measure conditioning performance in shampoo and conditioner applications. The combing performance of each shampoo formulation was measured within 24 hours of shampoo preparation, on two-three medium brown virgin European hair tresses and bleached versions of tresses prepared from the same medium brown hair stock (International Hair Importers, New Jersey). Prior to comb measurements, the tresses were treated with a solution of 4.5 wt % sodium lauryl sulfate (SLS), rinsed, and dried overnight at 23° C. and 50% relative humidity.

Combing performance was measured by applying the shampoo formulation to a 3 gram wt hair tress wet with water, at a ratio of 0.5 pbw shampoo/1 pbw hair tress, except for Examples 20A, 16a, and 27a in Table 5, and Examples 34a, 41a-d, and 46a in Table 6, where 0.1 pbw shampoo/1 pbw hair tress was applied. The tress was kneaded for 60 seconds, then rinsed with 35-40° C. water for 30 seconds. This process was repeated, then the tress was rinsed with deionized water and excess water squeezed from the tress. The tress was placed on the double comb apparatus and wet combing force measured 8 times on an Instron 5542 testing system at a cross head speed of 12.5 cm/min using the double comb method, with Ace hard rubber fine pocket combs, at 23° C. and 50% relative humidity. Hair tresses were then allowed to dry overnight at 23° C. and 50% relative humidity, and the dry comb performance was measured using the same double comb method. The comb energies in Table 5 represent the total wet and dry comb energy on both bleached hair and virgin brown hair.

In the nonsilicone shampoo formulation Examples 18, 19, and 23 in Table 5, the polymers in Comparative Examples 2 and 3 (Table 3) and the polymer of the invention in Example 7 (Table 3) demonstrated reduced wet and dry comb energies relative to the control shampoo containing no polymer in shampoo Example 16 in Table 5. In the nonsilicone shampoo formulations containing carbomer, Examples 20a, 27a, and 16a in Table 5, the polymer of the invention in Example 11c (Table 3) demonstrated reduced wet comb energy relative to the control shampoo containing no polymer and to the comparative control polymer in Example 4a, Table 3 in shampoo Examples 16a and 20a, respectively in Table 5.

In the silicone shampoo formulations in Table 6, the polymer of the invention in Example 41 demonstrated a significant reduction in wet comb energy on both bleached and virgin brown hair relative to the no polymer control shampoo in Example 46.

In the silicone shampoos containing carbomer, polymers of the invention in Examples 41a-d and the polymer in Comparative Example 34a demonstrated a significant reduction in wet comb energy on both bleached and virgin brown hair relative to the no polymer control shampoo in Comparative Example 46a.

Dry Hair Friction and Stiffness Measurement

Conditioning of dry hair is often described as a "silky-soft" feel to the hair. This sensory aspect can be deconvoluted in part using the following measurement. Using an apparatus disclosed in (K. A. Vaynberg, TRI Hair Care Symposium, September 2008), the work or energy to pull a tress through a zig-zag conformation is correlated to the stiffness and interfiber friction between hair fibers. Measurements performed in the free rotation mode are shown in the column labeled "Lubricity" in Table 6. These measurements represent friction against the pins and interfiber friction. The data demonstrate that the shampoo example of the invention, Example 41, dramatically improves hair lubricity on virgin brown hair, by reducing the frictional energy on these hair samples when compared with the Comparative Examples 31-33, 35 and with the no polymer control shampoo in Comparative Example 46.

The data in Table 6 also demonstrate that the shampoo examples of the invention, Examples 41a, b, c, and 41d, improves hair lubricity on virgin brown hair and bleached hair, by reducing the frictional energy on these hair samples when compared with the no polymer control shampoo in Comparative Example 46a.

In the silicone shampoo formulation Examples 31-35 in Table 6, the polymers in Comparative Examples 1-5 (Table 3) and in Examples 36-41 and 43-45, the polymers of the invention in Examples 6-11 and 13-15 (Table 3) demonstrate reduced wet and dry comb energies relative to the control shampoo containing no polymer in Comparative Example 46 in Table 6.

Table 6 contains the results of comb energy, silicone deposition, silicone distribution, and hair lubricity for polymers examples in Table 3 in a silicone shampoo containing the shampoo premix in Table 4, with and without added carbomer.

TABLE 6

| Example | Polymer in Table 3 Example | Silicone Shampoo Viscosity | Comb Energy on Bleached European medium brown Hair | | Silicone Deposited on Bleached European medium brown Hair Silicone/ppm | Comb Energy on European medium brown Virgin Hair | | Silicone Deposited on European medium brown Hair Silicone/ppm |
|---|---|---|---|---|---|---|---|---|
| | | | wet Comb E/gf-mm | Dry Comb E/gf-mm | | wet Comb E/gf-mm | Dry Comb E/gf-mm | |
| 31 | 1 | 4040 | 11593 | 1216 | 338 | 3635 | 3202 | 775 |
| 32 | 2 | 1580 | 14383 | 1369 | | 5095 | 5701 | |
| 33 | 3 | 3900 | 11879 | 1167 | 19 | 4441 | 6659 | 534 |
| 34 | 4 | 5400 | 14989 | 1085 | 98 | 3075 | 1698 | 2558 |
| 34a | 4a | 34200 | 6845 | | | 1592 | | |
| 35 | 5 | 2840 | 15442 | 1513 | | 3011 | 5794 | 997 |
| 36 | 6 | 3840 | 17919 | 1197 | | 4077 | 4677 | |
| 36a | 6a | 30900 | | | | | | |
| 37 | 7 | 4380 | 13863 | 1574 | 45 | 4239 | 7009 | 685 |
| 38 | 8 | 4300 | 16745 | 1256 | | 3798 | 4024 | |
| 39 | 9 | 4860 | 13065 | 1715 | 11 | 3825 | 4666 | 169 |
| 40 | 10 | 4800 | 12416 | 1367 | 80 | 3608 | 4443 | 701 |
| 41 | 11 | 5100 | 13254 | 1503 | | 2690 | 2086 | |
| 41a | 11a | 30300 | 8714 | | | 1712 | | |
| 41b | 11b | 26400 | 7020 | | | 1810 | | |
| 41c | 11c | 29100 | 7953 | | | 1661 | | |
| 41d | 11d | 36900 | 7577 | | | 1849 | | |
| 41e | 11e | 26800 | | | | | | |
| 42 | 11f | 26200 | | | | | | |
| 43 | 13 | 5260 | | | 185 | | | 216 |
| 44 | 14 | 4980 | | | | | | |
| 45 | 15 | 5760 | 11798 | | 20 | 4169 | | 146 |
| 46 | No Polymer Control | 1460 | 16218 | 1282 | <10 | 4824 | 4861 | <10 |
| 46a | carbomer-noPolymer | 10800 | 13824 | | | 2286 | | |

| Example | Virgin Brown Hair Aesthetics Sensory Feel V. Brown hair | Lubricity European bleached medium brown Hair gf-mm | Lubricity European medium brown Virgin Hair gf-mm | Virgin Brown Hair Silicone Distribution-Relative IR Ratio | | |
|---|---|---|---|---|---|---|
| | | | | root | middle | tip |
| 31 | Some conditioning | | 731 | 0.14 | <0.05 | <0.05 |
| 32 | Some conditioning/tangles | | 841 | <0.05 | <0.05 | <0.05 |
| 33 | Fly Away | | 776 | 0.07 | <0.05 | <0.05 |
| 34 | Very Conditioned/stringy | | | | | |
| 34a | Conditioned | 1947 | 1040 | | | |
| 35 | Fly-Away/Tangles | | 577 | 0.18 | 0.13 | 0.07 |
| 36 | Fly Away | | | 0.27 | 0.08 | 0.13 |
| 36a | | | | | | |
| 37 | Fly Away | | | 0.09 | 0.05 | 0.05 |
| 38 | | | | | | |
| 39 | | | | | | |
| 40 | Some conditioning | | 678 | 0.4 | 0.25 | 0.17 |
| 41 | Conditioned/Smooth/Silky | | 587 | 0.63 | 0.54 | 0.51 |
| 41a | Conditioned | 1833 | 1099 | | | |
| 41b | Conditioned | 1880 | 995 | | | |
| 41c | Smooth/Silky | 1973 | 1142 | | | |
| 41d | Smooth/Silky | 1799 | 1092 | | | |
| 41e | | | | | | |
| 42 | | | | | | |
| 43 | | | | | | |
| 44 | | | | | | |
| 45 | | | 1259 | | | |
| 46 | | | 960 | <0.05 | <0.05 | <0.05 |
| 46a | | 2179 | 1852 | | | |

Sensory Observations

The sensory feel and visual aspect of hair after a shampoo treatment with a conditioning shampoo is also a valued measurement of conditioning performance. This performance is described in Table 6 in the "sensory" column. Note that the Comparative shampoo Examples 31, 32 (Comparative Examples 1 and 0.2, Table 3) delivered some conditioning, and Comparative shampoo Example 34 (Comparative Example 4, Table 3) delivered good conditioning, however Comparative shampoo Examples 33 and 35 in Table 6 were perceived as having very little conditioning, and static buildup, as described by the fly-away characteristic.

The polymer of use in the invention in Example 40 in Table 6 (Polymer Example 10, Table 3) demonstrated some conditioning on virgin brown hair, and the polymer of use in the invention in Example 41 in Table 6 (Polymer Example 11 in Table 3) demonstrated excellent conditioning, as described by the "smooth and silky" descriptors. This performance was validated further with lubricity measurements, as described in the section on dry hair friction and stiffness measurements.

For the carbomer formulas in Table 6, the polymers of the invention in Examples 41a and b in Table 6 (Polymer Examples 11a, 11b, Table 3) demonstrated some conditioning on virgin brown hair, and the polymer of the invention in Example 41c and d in Table 6 (Polymer Example 11c and 11d in Table 3) demonstrated excellent conditioning, as described by the "smooth and silky" descriptors.

Silicone Deposition Measurements

Silicone deposition measurements are performed according to the following procedure:

The hair tress samples are extracted with methylene chloride, the solvent evaporated to dryness, then diluted to volume in deuterated chloroform. The silicone oil is quantitated using the $SiCH_3$ band near 1261 cm$^{-1}$. This method is valid for silicone oil levels in the 30 to 1800 ppm range. Sulfonates and sulfates will interfere with the measurement of the $SiCH_3$ band near 1261 cm$^{-1}$ at lower ppm values.

As shown in Table 6, shampoo formulations 31-35 in Table 6, (containing the polymers in Comparative Examples 1-5, Table 3) and shampoo formulation Examples 36-41, 43, and 45 in Table 5 (the polymers of the invention in Examples 6-11, 13 and 15 in Table 3) demonstrate good silicone deposition on virgin brown and bleached hair relative to the control shampoo containing no polymer in Comparative Example 46.

Using attenuated total reflectance measurements on bundles of the hair fibers from each tress, it is also possible to map the deposition profile of silicone along a tress according to the following method:

A small portion of the hair tress was cut approximately one inch below the wax holder. The top and bottom sections were secured with a small amount of tape to keep the tress together. Infrared spectra were collected near the top, middle and bottom sections of the hair tress. The peak height of the silicone band near 796.5 cm$^{-1}$ (tangent baseline) was ratioed to a reference band area slice 940.1 cm$^{-1}$ to 919.9 cm$^{-1}$ (tangent baseline) to determine the relative surface silicone level.

All spectra were collected employing a Golden Gate diamond ATR mounted in a Nicolet Magna 760 FTIR spectrometer. The resolution was set to 4 cm$^{-1}$ and a collection time of 2 minutes 30 seconds.

At this time it is believed that the lowest detection level for this technique is a RSSL value of 0.05. All values below this will be reported as none detected.

The result is expressed as a ratio of the Si—CH$_3$ stretch/keratin absorbance to obtain an IR ratio profile along the length of the fiber, from the root end of the fiber to the tip end. Concentration of silicone can be measured with this method, with a ratio greater than 1 indicating the presence of a substantial amount of silicone. As shown in Table 6, the shampoo Examples 31-33 containing the polymers in Comparative Examples 1-3, Table 3, show little to no spread of silicone along the hair fiber. If observed, the silicone is located primarily at the root end of the tress, where the ratio is <0.2.

In the shampoo Examples 36, 40, and 41 in Table 6, containing the polymers of the invention in Examples 6, 10, 11, Table 3, the ratio exceeds a value of 0.2 along the tress for Example 11, and exceeds the 0.2 value for the tresses treated with the shampoo containing the polymer composition in Example 10. These results demonstrate the improved spread of silicone along the tress length, even to the more damaged tip regions, when using a cleansing formulation containing the polymers of the invention.

Zinc Deposition Measurements

Zinc deposition is preferred to be maximized onto the scalp, rather than onto the hair. Samples of VitroSkin® artificial skin (available from IMS Testing Group,) were used as the skin mimic substrate.

A commercial antidandruff shampoo formulation containing zinc pyrithione and zinc carbonate (Head and Shoulders® shampoo was used for these determinations). The improved zinc deposition of the polymers of the invention is demonstrated by 1:1 dilution of the shampoo with a 0.4% solution of the polymer to be tested. This same type of dilution was then performed using isolation of the coacervate phase as the diluted sample is applied to a section of artificial skin (Vitro-Skin® artificial skin), followed by rinsing. The skin sample is then air dried overnite, then submitted for analysis by X-ray fluorescence to quantify zinc on the surface of the skin. The ppm Zinc as well as the zinc in micrograms/sq cm is given as output. The values for zinc measured were verified by then ashing the skin sample in the ICP instrument and measuring elemental zinc in the sample. This ICP data compared well with the XRAY fluorescence data.

The results of zinc deposition performance for polymers in Table 3 mixed with a commercial shampoo formulation (Head and Shoulders® shampoo) are set forth in Table 7.

TABLE 7

| Example | Polymer in Table 3 Example | Zn (ugram/sq cm) on vitro skin |
|---|---|---|
| 47 | 1 | 1.85 |
| 48 | 10 | 1.915 |
| 49 | No Polymer Control | 1.68 |

The zinc deposition performance of the comparative control in Example 47 and the commercial shampoo alone in Example 49 are shown in Table 7. As shown in Table 7, the zinc deposition performance of the polymer of the invention in Example 48 is improved relative to the commercial shampoo control Example 49 and the comparative polymer control in Example 47.

A model antidandruff shampoo was prepared comprised of the formula in Table 8 according to a procedure referenced in US2007/0128147, incorporated herein by reference in its entirety. As shown in Table 9, the shampoo in Example 51 containing the polymer of the invention, Example 11a, Table 1, reduced both the wet and dry comb energy needed to comb through virgin brown hair compared with the commercial shampoo in Example 50.

TABLE 8

| Model Antidandruff Shampoo | | Shampoo parts per hundred | 100 g Shampoo | premix prep order of addition |
|---|---|---|---|---|
| Water | | 74.39 | 0.63 | 1 |
| SLES | Standapol ES2 | 10.00 | 39.0 | 2 |
| SLS | Rhodapon LCP | 6.00 | 20.20 | 3 |
| Cetyl alcohol | Crodacol C-95 NF | 0.60 | 0.60 | 5 |
| Cocamide MEA | Ninol CMP | 0.80 | 0.80 | 6 |
| Glycol distearate | Lexemul EGDS | 1.50 | 1.50 | 7 |
| Silicone preemulsion | Dow Corning 2-1490 | 1.48 | 3.5 | 11 |
| ZPT | Zinc Omadine FPS-Arch Chemical | 1.00 | 2.08 | 10 |
| Zinc Carbonate | Brueggeman Chemical | 1.61 | 1.61 | 13 |
| Hydrochloric acid(6N) | | 0.18 | 0.18 | 4 |
| Magnesium Sulfate | | 0.28 | 0.28 | 9 |
| 25% sodium chloride | | 1.00 | 4.00 | 14 |
| Polymer | | 0.50 | 25.00 | 12 |
| Germaben II | Germaben II | 0.66 | 0.66 | 8 |
| | | 100.00 | 100.0 | |

Foam stability and foam denseness, richness of shampoo formulations can be measured using lather drainage tests. Foam stability of the lather from the shampoo in Example 51 was measured according to the following procedure:

Standard Procedure

Lather Drainage Time

The objective of this test is to measure the lather drainage time of a diluted surfactant solution. Long drainage times indicate a rich, dense lather with good stability.
Equipment:
  Waring Blender Model #7012 or #34BL97 or equivalent
  Funnel, preferably plastic; 6" diameter, 7/8" ID neck, 5¼" high, with a horizontal wire 2" from the top.
  U.S.A. Standard Testing Sieve No. 20 or Tyler Equivalent 20 mesh or 850 micrometer or 0.0331 inch sieve. Sieve, preferably over 7 inches in diameter but a smaller size could also be used.
  Stopwatch or a timer.
  Water-bath
  Thermometer
Procedure:
1. The formulation was prepared by mixing 66.45 g shampoo Example 50 and 51 with 933.55 g of deionized water in a large beaker.
2. 200 grams of diluted solution were weighed for each measurement.
3. The test was run at a controlled temperature, 25° C. by placing 200 g of this solution (in a capped 8 oz. jar) in a water bath set to the desired temperature, for 2 hours.
4. The lather drainage time for each solution was measured according to the following procedure. A total of 3 measurements were made for each formulation.
a. Pour 200 g of solution into a clean, dry Waring blender glass vessel.
b. Whip on the highest speed for exactly 1 minute while covered.
c. Immediately pour the foam into a clean, dry funnel standing on a 20 mesh screen over a beaker.
d. Pour the foam from the blender for exactly 15 seconds. Try to get as much foam as possible into the funnel without overflowing. Stop pouring after 15 seconds. Keep the stopwatch running.
e. Note the total time needed for the foam to drain (including the 15 seconds of pour time) so that the wire is no longer covered by foam or liquid.

The lather/foam prepared from the shampoo in Example 51 containing the polymer of the invention was significantly more stable and richer foam than the foam prepared from the commercial shampoo in Example 50, as shown by the longer drainage time for the foam from Example 51.

Although the invention has been described with referenced to preferred embodiments, it is to be understood that variations and modifications in form and detail thereof may be made without departing from the spirit and scope of the claimed invention. Such variations and modifications are to be considered within the purview and scope of the claims appended hereto.

What is claimed:

1. A cleansing composition comprising, a surfactant, a polymer composition and a solvent wherein the polymer composition comprises a non-cellulosic cationically modified polysaccharide, wherein the cationic modification comprises a mixture of at least two quaternary ammonium groups having different combinations of alkyl, aryl, or aralkyl substituents, and wherein the quaternary ammonium groups are attached to the non-cellulosic polysaccharide via an ether or urethane linkage.

2. The cleansing composition of claim 1 wherein the non-cellulosic cationically modified polysaccharide comprises a polygalactomannan.

3. The cleansing composition of claim 1 wherein the non-cellulosic cationically modified polysaccharide comprises a polyglucomannan.

4. The cleansing composition of claim 1 wherein the non-cellulosic canonically modified polysaccharide comprises a polyglucose.

5. The cleansing composition of claim 4 wherein the polyglucose is starch.

6. The cleansing composition of claim 1 wherein the non-cellulosic cationically modified polysaccharide comprises a polyaminoglycan.

7. The cleansing composition of claim 6 wherein the polyaminoglycan is chitosan.

8. The cleansing composition of claim 2 wherein the polygalactomannan is selected from the group consisting of guar, cassia, fenugreek, locust bean, tara gum, honey locust, and flame tree.

9. The cleansing composition of claim 2 wherein the polygalactomannan comprises guar.

10. The cleansing composition of claim 1 wherein the non-cellulosic cationically modified polysaccharide is selected from the group consisting of xanthan gum, gellan gum, welan gum, rhamsan gum, konjac mannan, gum arabic, soy polysaccharide, xylofructose gums and tamarind gum.

11. The cleansing composition of claim 1 wherein the non-cellulosic cationically modified polysaccharide has a cationic degree of substitution (DS) in a range with a lower limit of about 0.0001 DS and an upper limit of about 3.0 DS for each of the least two quaternary ammonium groups.

12. The cleansing composition of claim 1 wherein the non-cellulosic cationically modified polysaccharide has a

TABLE 9

| Example | Polymer Example (Table 1) | Comb Energy Virgin Brown Hair | | Sensory Rinse | Sensory Dry | Lather Stability Seconds |
| | | Wet Comb/gf-mm | Dry Comb/gf-mm | | | |
| --- | --- | --- | --- | --- | --- | --- |
| 50 | Commercial Shampoo[a] | 4745 | 3557 | Easy rinse | Not conditioned | 11 |
| 51 | 11a | 3889 | 3344 | Easy rinse | Very Conditioned | 119 |

[a]Head & Shoulders ® Smooth & Silky cationic degree of substitution (DS) with a lower limit of about 0.001 DS for each of the least two quaternary ammonium groups.

13. The cleansing composition of claim 1 wherein the non-cellulosic cationically modified polysaccharide has a cationic degree of substitution (DS) with an upper limit of about 1.0 DS for each of the least two quaternary ammonium groups.

14. The cleansing composition of claim 1 wherein the non-cellulosic cationically modified polysaccharide has a weight average molecular weight (Mw) with a lower limit of about 10,000 and an upper limit of about 2,000,000.

15. The cleansing composition of claim 14 wherein the non-cellulosic cationically modified polysaccharide has a weight average molecular weight (Mw) with a lower limit of about 200,000 and an upper limit of about 1,500,000.

16. The cleansing composition of claim 15 wherein the non-cellulosic cationically modified polysaccharide has a weight average molecular weight (Mw) with a lower limit of about 300,000 and an upper limit of about 1,000,000.

17. The cleansing composition of claim 1 wherein the cationic modification comprises a mixture of at least two quaternary ammonium groups having different combinations of alkyl group substituents.

18. The composition of claim 17 wherein the alkyl group substituents have an alkyl chain length in a range from one carbon to thirty carbons.

19. The cleansing composition of claim 18 wherein the alkyl group substituents on a first quaternary ammonium group comprise an alkyl chain length of one carbon.

20. The cleansing composition of claim 18 wherein each alkyl group substituent on the first quaternary ammonium group has an alkyl chain length of one carbon.

21. The cleansing composition of claim 18 wherein the alkyl group substituents on a second quaternary ammonium group comprise an alkyl chain length in a range from one carbon to thirty carbons.

22. The cleansing composition of claim 21 wherein the alkyl group substituents on the second quaternary ammonium group have an alkyl chain length greater than 2 carbons.

23. The cleansing composition of claim 21 wherein the alkyl group substituents on the second quaternary ammonium group comprise an alkyl chain length of twelve carbons.

24. The cleansing composition of claim 21 wherein the alkyl group substituents on the second quaternary ammonium group comprise an alkyl chain length of eighteen carbons.

25. The cleansing composition of claim 21 wherein the alkyl group substituents on the second quaternary ammonium group comprise an alkyl chain length of twenty-two carbons.

26. The cleansing composition of claim 21 wherein the non-cellulosic cationically modified polysaccharide comprises a polygalactomannan.

27. The cleansing composition of claim 26 wherein the polygalactomannan is selected from the group consisting of guar, cassia, fenugreek, locust bean, tam gum, honey locust, and flame tree.

28. The cleansing composition of claim 27 wherein the polygalactomannan comprises guar.

29. The cleansing composition of claim 27 wherein the polygalactomannan comprises cassia gum.

30. The cleansing composition of claim 29 wherein the polygalactomannan comprises fenugreek.

31. The cleansing composition of claim 22 wherein the non-cellulosic cationically modified polysaccharide comprises a starch.

32. The cleansing composition of claim 1, wherein the surfactant is selected from the group consisting of amphoteric surfactants, anionic surfactants, nonionic surfactants, zwitterionic surfactants, and mixtures thereof.

33. The cleansing composition of claim 1 further comprising one or more additional ingredients selected from preservatives, thickeners, functional polymers, viscosity modifiers, electrolytes, pH adjusting agents, fragrances, dyes, UV screens, organosilicone materials, antidandruff agents, vitamins, vitamin derivatives, colors, antiviral, antifungal, or antimicrobial agents.

34. The cleansing composition of claim 1 wherein the cleansing composition comprises a personal care composition.

35. The cleansing composition of claim 34 wherein the personal care composition is a hair care composition.

36. The cleansing composition of claim 23 wherein the personal care composition is a skin care composition.

37. The cleansing composition of claim 21 wherein the cleansing composition comprises a personal care composition.

38. The cleansing composition of claim 37 wherein the personal care composition is a hair care composition.

39. The cleansing composition of claim 37 wherein the personal care composition is a skin care composition.

40. The cleansing composition of claim 21 wherein the cleansing composition comprises a household care composition.

41. The cleansing composition of claim 40 wherein the household care composition is a fabric care composition.

42. The cleansing composition of claim 40 wherein the household care composition is a hard surface cleaner composition.

43. The cleansing composition of claim 1 wherein the quaternary ammonium groups are attached to the non-cellulosic polysaccharide via an ether linkage.

44. The cleansing composition of claim 1 wherein the quaternary ammonium groups are attached to the non-cellulosic polysaccharide via an urethane linkage.

* * * * *